(12) United States Patent
Huang et al.

(10) Patent No.: US 11,726,195 B2
(45) Date of Patent: Aug. 15, 2023

(54) ULTRASOUND SYSTEMS AND METHODS FOR MEASURING ACOUSTIC ATTENUATION COEFFICIENTS

(71) Applicant: KONINKLIJKE PHILIPS N.V., Eindhoven (NL)

(72) Inventors: Sheng-Wen Huang, Ossining, NY (US); Hua Xie, Cambridge, MA (US); Jean-Luc Francois-Marie Robert, Cambridge, MA (US); Man Nguyen, Melrose, MA (US); Vijay Thakur Shamdasani, Kenmore, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 640 days.

(21) Appl. No.: 16/648,010

(22) PCT Filed: Sep. 6, 2018

(86) PCT No.: PCT/EP2018/073962
§ 371 (c)(1),
(2) Date: Mar. 17, 2020

(87) PCT Pub. No.: WO2019/057503
PCT Pub. Date: Mar. 28, 2019

(65) Prior Publication Data
US 2020/0256971 A1    Aug. 13, 2020

Related U.S. Application Data

(60) Provisional application No. 62/560,248, filed on Sep. 19, 2017.

(51) Int. Cl.
*G01S 7/52* (2006.01)
*A61B 8/00* (2006.01)
*G01N 29/11* (2006.01)
*G01S 15/89* (2006.01)
(Continued)

(52) U.S. Cl.
CPC ............ *G01S 7/52085* (2013.01); *A61B 8/58* (2013.01); *G01H 3/125* (2013.01); *G01H 9/002* (2013.01);
(Continued)

(58) Field of Classification Search
CPC ............ G01S 7/52085; G01S 7/52036; G01S 15/895; G01S 15/8959; G01N 29/11;
(Continued)

(56) References Cited

U.S. PATENT DOCUMENTS 4,564,019 A    1/1986    Miwa
4,574,635 A    3/1986    't Hoen
(Continued)

FOREIGN PATENT DOCUMENTS

CN    105954353 A   *   9/2016   ............ G01N 29/00
CN    205786484 U   *  12/2016
JP    S63194644 A        8/1988

OTHER PUBLICATIONS

Dines et al: "Ultrasonic Attenuation Tomography of Soft Tissues"; Ultrasonic Imaging, vol. 1, No. 1, 1979, pp. 16-33.
(Continued)

*Primary Examiner* — Lisa M Caputo
*Assistant Examiner* — Rose M Miller

(57) ABSTRACT

Systems and methods for improving spectral-shift methods for calculating acoustic attenuation coefficients are disclosed. Systems, methods, and apparatuses for transmitting ultrasound pulse sequences for improved signal-to-noise outside the main passband of ultrasound transducers are disclosed. Systems, methods, and apparatuses for using the echoes from the transmitted pulse sequences to calculate the attenuation coefficient are disclosed.

19 Claims, 5 Drawing Sheets

(51) Int. Cl.
  *G01H 3/12*  (2006.01)
  *G01H 9/00*  (2006.01)
  *G01N 29/24* (2006.01)
  *G01N 29/34* (2006.01)

(52) U.S. Cl.
  CPC ......... *G01N 29/11* (2013.01); *G01N 29/2406* (2013.01); *G01N 29/2437* (2013.01); *G01N 29/343* (2013.01); *G01S 7/52036* (2013.01); *G01S 15/895* (2013.01); *G01N 2291/015* (2013.01); *G01N 2291/02475* (2013.01); *G01S 15/8959* (2013.01)

(58) Field of Classification Search
  CPC ........... G01N 29/2406; G01N 29/2437; G01N 29/343; G01N 2291/015; G01N 2291/02475; A61B 8/58; G01H 3/125; G01H 9/022
  USPC ........................................................ 600/443
  See application file for complete search history.

(56) References Cited

U.S. PATENT DOCUMENTS

| | | | |
|---|---|---|---|
| 4,621,645 A | 11/1986 | Flax | |
| 4,646,748 A | 3/1987 | Fujii et al. | |
| 5,361,767 A | 11/1994 | Yukov | |
| 5,663,502 A * | 9/1997 | Nagashima | G01N 29/46 702/171 |
| 8,652,048 B2 * | 2/2014 | Skerl | G16H 50/30 600/407 |
| 2002/0010399 A1 | 1/2002 | Konofagou et al. | |
| 2008/0221449 A1 | 9/2008 | Sato | |
| 2013/0345565 A1 | 12/2013 | Fan et al. | |

OTHER PUBLICATIONS

Kak et al: "Signal Processing of Broadband Pulsed Ultrasound:Measurement of Attenuation of Soft Biological Tissues"; IEEE Transactions on Biomedical Engineerign, vol. BME-25, No. 4, Jul. 1978, pp. 321-344.

Kuc: "Estimating Acoustic Attenuation From Reflected Ultrasound Signals: Comparison of Spectral-Shift and Spectral-Difference Approaches"; IEEE Transactions on Acoustics, Speech, and Signal Processing, vol. ASSP-32, No. 1, Feb. 1984, pp. 1-6.

PCT/EP2018/073962, ISR & WO, Nov. 28, 2018, 17 page Document.

* cited by examiner

ULTRASOUND SYSTEMS AND METHODS FOR MEASURING ACOUSTIC ATTENUATION COEFFICIENTS

CROSS-REFERENCE TO PRIOR APPLICATIONS

This application is the U.S. National Phase application under 35 U.S.C. § 371 of International Application No. PCT/EP2018/073962, filed on Sep. 6, 2018, which claims the benefit of U.S. Provisional Patent Application No. 62/560,248, filed on Sep. 19, 2017. These applications are hereby incorporated by reference herein.

TECHNICAL FIELD

This application is directed to ultrasound systems and methods for measuring acoustic attenuation coefficients. Specifically, this application is directed to measuring acoustic attenuation coefficients in materials with ultrasound transducers.

BACKGROUND

Measurement of attenuation coefficients in tissues (e.g., longitudinal attenuation coefficients) has long been an academic research topic. In addition to potential of characterizing tissue based on attenuation coefficient, knowledge about the attenuation coefficient is a starting point for extracting other properties of tissue such as backscatter coefficient. Recently, attenuation coefficient has also gained interest from the medical ultrasound industry. For example, fat is a more attenuative medium to ultrasound than normal liver tissue, thus, attenuation coefficient could serve as a biomarker for fatty liver quantification.

Accurate estimation of attenuation coefficient is a difficult task unless the imaged object is very homogeneous, as both absorption and scattering properties of the object contribute to signal level variation with depth. Furthermore, transducer impulse response and other system-dependent factors may influence attenuation coefficient measurements.

SUMMARY

The present invention provides systems and methods for measuring attenuation coefficients of a target object, e.g., tissue, over large usable frequency ranges, thereby reducing noise and other signal degradation factors to improve tissue characterization and generally enable improved medical diagnosis.

The disclosure describes ultrasound systems and methods which employ spectral-shift techniques with enhanced signal to noise ratio over a wide frequency range. Particularly, the systems and methods described herein may provide improved performance of spectral-shift methods by firing pulses that can provide good signal-to-noise ratio over a wide frequency range. For example, a system according to the present disclosure may use wideband pulses to cover the main passband of the transducer, and narrowband pulses with higher and/or lower center frequencies may be fired separately, which may ensure good signal quality at those frequencies.

According to some embodiments of the present disclosure, a method for determining an attenuation coefficient of tissue may include transmitting ultrasound pulses from an ultrasound transducer towards a tissue in accordance with a pulse sequence, the pulse sequence including pulses of at least one first frequency inside and at least one second frequency outside a main passband of the ultrasound transducer, receiving echo signals that correspond to the pulses of the at least one first and the at least one second frequencies of the pulse sequence, determining an attenuation coefficient of the tissue based, at least in part, on a combination of received echo signals that correspond to the pulses of the at least one first and the at least one second frequencies, and displaying an ultrasound image concurrently with the calculated attenuation coefficient.

According to some embodiments of the present disclosure, an ultrasound imaging system may include an ultrasound transducer that may be configured to transmit ultrasound pulses toward a tissue, wherein the ultrasound pulses may be transmitted in accordance with a pulse sequence, the pulse sequence may include pulses of at least one first frequency inside and at least one second frequency outside a main passband of the ultrasound transducer. The ultrasound imaging system may include an attenuation coefficient calculator that may be configured to calculate an attenuation coefficient of the tissue based, at least in part, on echo signals that correspond to the pulses of the at least one first and the at least one second frequencies, and at least one processor configured to generate ultrasound imaging data based on the echo signals.

DETAILED DESCRIPTION

Figure 1:
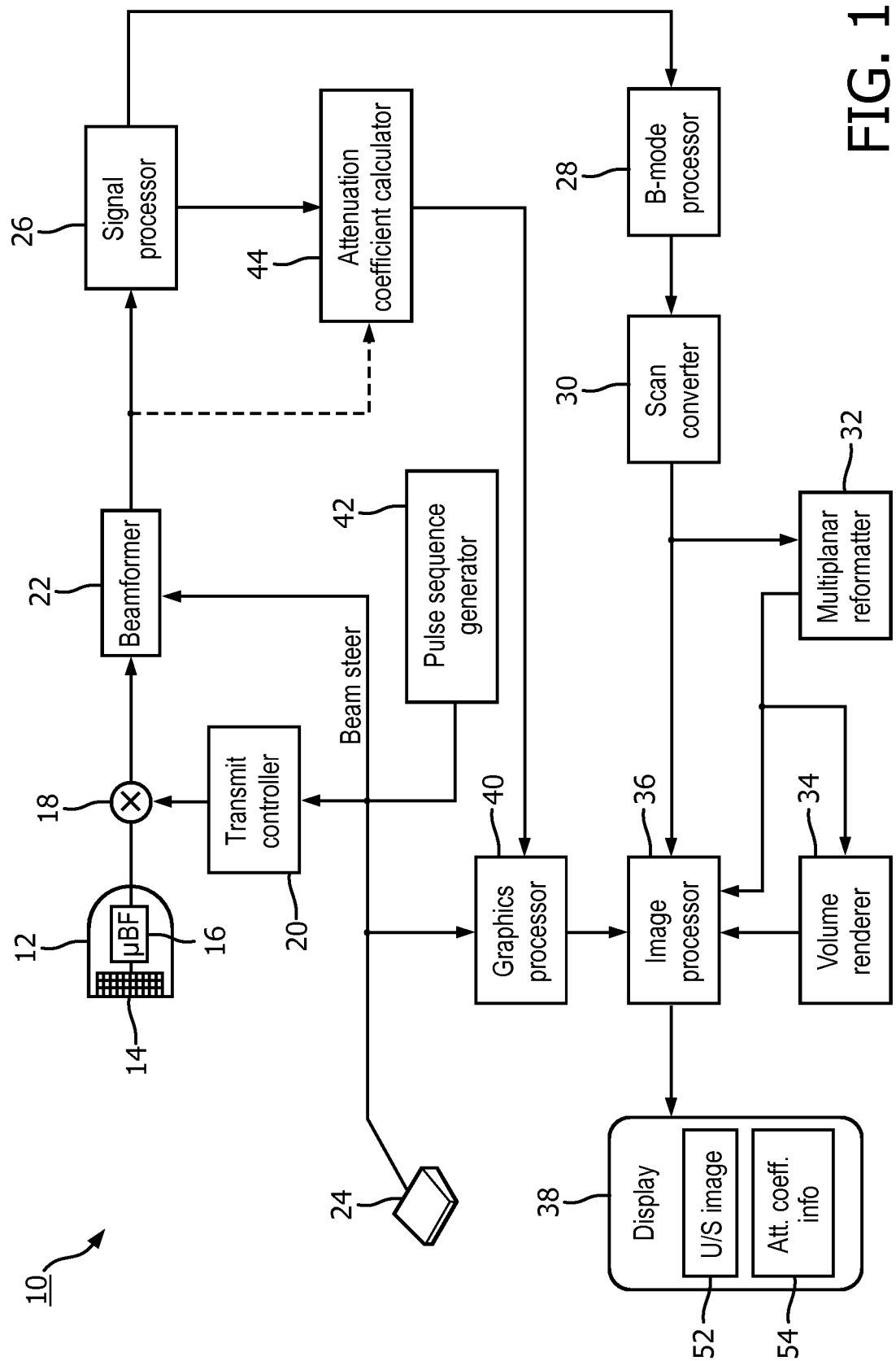
FIG. 1 is a block diagram of an ultrasound imaging system according to an embodiment of the disclosure.

The following description of embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system.

The following detailed description is therefore not to be taken in a limiting sense, and the scope of the present system is defined only by the appended claims. The leading digit(s) of the reference numbers in the figures herein typically correspond to the figure number, with the exception that identical components which appear in multiple figures are identified by the same reference numbers. Moreover, for the purpose of clarity, detailed descriptions of certain features will not be discussed when they would be apparent to those with skill in the art so as not to obscure the description of the present system.

As previously noted, the accurate estimation of attenuation coefficient is a challenging task, especially in non-homogeneous tissue. To attempt to estimate attenuation coefficient, many technically sound methods rely on information in the power spectra of echo signals after equalization using a homogeneous reference phantom to suppress effects of transducer impulse response and diffraction. Let $S_{ref}(f; x, z)$ denote the power spectrum of the reference phantom at temporal frequency $f$, lateral position x and depth z, and $S_{obj}(f; x, z)$ that of the imaged object. The equalized power spectrum at (x, z) is:

$$\Phi(f; x, z) = \frac{S_{obj}(f; x, z)}{S_{ref}(f; x, z)}. \quad \text{Equation (1)}$$

When the imaged object is homogeneous, it is often assumed, by ignoring difference in dependency of backscatter coefficient on frequency between the reference phantom and the imaged object, that:

$$\Phi(f;x,z) \cong A \exp[-4fz(\alpha_{obj}-\alpha_{ref})], \quad \text{Equation (2)}$$

where $\alpha_{obj}$ is attenuation coefficient of the imaged object, $\alpha_{ref}$ is the attenuation coefficient of the reference phantom, and A is a constant. In this case, one can estimate $\alpha_{obj}$ as follows:

$$\alpha'_{obj}(x, z) = \alpha_{ref} - \frac{\int_{f_1}^{f_2} w(f) f^{-1} \beta(f; x, z) df}{4 \int_{f_1}^{f_2} w(f) df} \quad \text{Equation (3)}$$

where $w(f)$ is a weighting function, and $$\beta(f; x, z) = \frac{\partial \ln \Phi(f; x, z)}{\partial z}. \quad \text{Equation (4)}$$

Other variants to the above method exist. Such methods do not really solve $\alpha_{obj}$ based on an assumption on linear relationship between attenuation in dB and frequency, as these methods can apply $\Phi(f; x, z)$ at only one frequency $f_0$:

$$\alpha'_{obj}(x, z) = \alpha_{ref} - \frac{\partial \ln \Phi(f_0; x, z)}{4 f_0 \partial z}. \quad \text{Equation (5)}$$

The method above and variants thereof are referred to as spectral-difference methods. Spectral-difference methods do not handle the situation of depth-dependent A well, which may occur when the imaged object is inhomogeneous, as now $$\frac{\partial A}{\partial z}$$

can be part of $\alpha_{obj}'$, causing bias in the calculation of the attenuation coefficient. A method for determining the attenuation coefficient that is robust against depth-dependent A and provides a more accurate measurement of the attenuation coefficient is desired. Accurate measurements of attenuation coefficient may allow this factor to be used for medical diagnosis and/or monitoring, such as fatty liver quantification.

To avoid the bias in attenuation coefficient measurements caused by spectral-difference methods, for attenuation coefficient estimation in soft tissues, the linear dependency of $g(f; x, z) = \ln \Phi(f; x, z)$ on $f$ (temporal frequency) is often used. In this case, one can estimate $\alpha_{obj}$ (attenuation coefficient of an imaged object) as follows:

$$\alpha''_{obj}(x, z) = \alpha_{ref} - \frac{\partial}{4\partial z}\left\{\frac{\partial}{\partial f} \ln \Phi(f; x, z)\right\}. \quad \text{Equation (6)}$$

Where $\alpha_{ref}$ is the attenuation coefficient of the reference phantom, and x and z are the lateral position and depth, respectively. An alternative equivalent to the last formula is to estimate down-shift of center frequency assuming Gaussian-shaped bandpass spectra. These methods based on the linear relationship between g and $f$ are referred to as spectral-shift methods.

The inventors have recognized that the spectral-shift methods may be more practical for in vivo imaging because they are less sensitive to variation in backscatter coefficient. However, spectral-shift methods are generally more sensitive to speckle noise and thermal noise because of their second order partial differential nature. To evaluate improvements in the accuracy of spectral-shift methods, a technique which derives the Cramér-Rao bound for the variance of spectral-shift-based estimators may be used. It can be shown accordingly that, assuming the use of the frequency range $[f_1, f_2]$, $$\text{variance} \geq \frac{C}{(f_2 - f_1)^3}, \quad \text{Equation (7)}$$

where C is independent of temporal frequency. Based on such analysis, the inventors have recognized that in order to reduce error in attenuation coefficient estimates, a wider bandwidth should be used for ultrasound signals. For example, by increasing bandwidth by 50%, variance can be reduced by 70%. Increasing bandwidth may improve estimation accuracy of spectral-difference methods as more information can be used in Equation (3) as well as that of hybrid methods involving both spectral-difference and spectral-shift methods.

In accordance with principles of the present invention, ultrasound systems and methods, which use more frequency components in the equalized power spectrum (e.g., $\Phi(f; x, z) = S_{obj}(f; x, z)/S_{ref}(f; x, z)$) to estimate the attenuation coefficient are described, which may reduce errors, especially in spectral-shift methods. However, as transducers are band-limited, at frequencies where $S_{ref}(f; x, z)$ is small, the equalized power spectrum, $\Phi(f; x, z)$, may be dominated by noise. Thus, it may be more desirable for $f_2$ and $f_1$ to be within the main passband (e.g., −3 dB passband, −6 dB passband) of the transducer when imaging with conventional pulse sequences, limiting the bandwidth used for estimating the attenuation coefficient. To improve estimation accuracy, the present invention provides techniques for reducing noise such that $f_2$ and $f_1$ may be outside the main passband.

According to principles of the present disclosure, an ultrasound system may include a transducer array, which may be configured to transmit ultrasound pulses, for example under the control of a transmit/receive controller, according to commands for a pulse sequence (or simply sequence) generated by a pulse sequence generator. The sequence may be configured to improve the performance of spectral-shift methods, e.g., by providing improved signal-to-noise ratio (SNR) over a wide frequency range, such as by controlling the transmission of pulses as described herein. For example, the ultrasound system may be configured to transmit, e.g., for purposes of attenuation coefficient calculations, ultrasound pulses according to a sequence that includes one or more wideband pulses such as to cover the main passband or a portion of the main passband of the transducer, and one or more narrowband pulses with higher center frequencies, where the narrowband pulses may be transmitted separately from the wideband pulse(s). In some examples, the system may be configured to use narrowband pulses with low center frequencies. Transmitting narrowband pulses separately from the wideband pulses may allow for more energy to be applied to transducer elements to improve the strength of the ultrasound pulse at a higher or lower center frequency. Additionally or alternatively, transmitting narrowband pulses separately from the wideband pulses may allow for the narrowband pulses to be applied for a different length of time (e.g., longer period of time) than the wideband pulse. In this manner, the system may be configured to improve the SNR for signals generated by frequencies near the edge or outside of the main passband of the transducer, e.g., by adjusting the strength and duration of the narrowband pulses, which may in turn allow the resulting signals to be used to broaden the frequency range and reduce variance when estimating the attenuation coefficient.

In addition, systems of the invention configured to transmit pulse sequences for measuring the attenuation coefficient as described herein, may also transmit, before or after said pulse sequence, another ultrasound pulse sequence and/or sequences for B-mode or other type of imaging. That is, in some embodiments, the transducer of the system may be controlled to fire pulses according to a first sequence (e.g., for generating imaging data) and be further controlled to fire pulses according to a second sequence (e.g., for calculating attenuation coefficient(s) of the imaged region). In some embodiments, individual pulses of the first and second pulse sequences applied for measuring the attenuation coefficient and imaging may be applied in an interleaved manner.

An ultrasound system in accordance with some embodiments may include an ultrasound transducer, a transmit controller, and a pulse sequence generator operatively coupled to the transmit controller and configured to generate commands corresponding to a pulse sequence, which includes one or more pulses with frequencies inside a main passband of the ultrasound transducer and one or more pulses with frequencies outside a main passband of the ultrasound transducer, and transmit the commands to the transmit controller to cause the ultrasound transducer to transmit ultrasound pulses in accordance with the pulse sequence. In some embodiments, the system may further include an attenuation coefficient calculator configured to calculate an attenuation coefficient based, at least in part, on received echo signals resulting from the pulse sequence. In some embodiments, the ultrasound transducer may transmit another sequence, and echo signals responsive to this sequence may be used to generate ultrasound imaging data.

Referring to FIG. 1, an ultrasound imaging system 10 constructed in accordance with the principles of the present disclosure is shown in block diagram form. In the ultrasonic diagnostic imaging system of FIG. 1, an ultrasound probe 12 includes a transducer array 14 (or simply transducer 14) for transmitting ultrasonic waves and receiving echo information. The transducer array 14 may be any of a variety of known transducer arrays in the art, e.g., linear arrays, convex arrays or phased arrays. The transducer array 14, for example, can include a two dimensional array (as shown) of transducer elements capable of scanning in both elevation and azimuth dimensions for 2D and/or 3D imaging. Also, while described as included in a probe 12, which may be an external probe or an intraluminal probe, in some embodiments, the array 14 may be provided in a single or multi-patch arrangement within an enclosure configured to be conformally applied to a surface of a subject to be imaged.

The transducer 14 may be frequency band-limited. The frequency band of the transducer 14 may be based on mechanical and/or electrical properties of the transducer 14. The properties of the transducer 14 may be selected based, at least in part, on the imaging application. Medical imaging applications typically use frequencies between 1 MHz and 20 MHz. Transducers with lower center frequencies may be used for deep imaging while transducers with higher center frequencies may be used for superficial imaging. For example, for abdominal imaging, a transducer may have a frequency range of 1 MHz to 5 MHz. The main passband of the transducer may be 2 MHz wide (e.g., 2 MHz-4 MHz) with a center frequency of 3 MHz. This is only one example to illustrate the principles of transducer frequency range, main passband, and center frequency. It is understood that a wide variety of ultrasound transducers exist and which have a variety of frequency properties including, but not limited to, different sensitivities, center frequencies, frequency range widths, and main passband widths. The provided examples should not be interpreted to be limiting of the principles of the present disclosure, rather the principles described herein could be applied to virtually any type of transducer with its particular main passband and other properties.

Capacitive micro-machined ultrasound transducers (CMUT) may provide higher bandwidths than piezoelectric transducers. In some applications, CMUT may be preferred for measuring acoustic attenuation coefficient. However, piezoelectric transducers may have greater sensitivity. Accordingly, principles of the present disclosure may also be equally applied to different transducer types (e.g., CMUT or piezoelectric transducers).

In the illustrated example, the transducer array 14 is coupled to a microbeamformer 16 in the probe 12 which controls transmission and reception of signals by the transducer elements in the array. In this example, the microbeamformer is coupled by the probe cable to a transmit/receive (T/R) switch 18, which switches between transmission and reception and protects the main beamformer 22 from high energy transmit signals. In some embodiments, the T/R switch 18 and other elements in the system can be included in the transducer probe rather than in a separate ultrasound system base. The transmission of ultrasonic beams from the transducer array 14 under control of the microbeamformer 16 is directed by the transmit controller 20 coupled to the T/R switch 18 and the beamformer 22, which receives input from the user's operation of the user interface or control panel 24. One of the functions controlled by the transmit controller 20 is the direction in which beams are steered. Beams may be steered straight ahead from (orthogonal to) the transducer array, or at different angles for a wider field of view. The partially beamformed signals produced by the microbeamformer 16 are coupled to a main beamformer 22 where partially beamformed signals from individual patches of transducer elements are combined into a fully beamformed signal.

The beamformed signals are coupled to a signal processor 26. The signal processor 26 can process the received echo signals in various ways, such as bandpass filtering, decimation, I and Q component separation, and harmonic signal separation. The signal processor 26 may also perform additional signal enhancement such as speckle reduction, signal compounding, and noise elimination. The processed signals are coupled to a B mode processor 28, which can employ amplitude detection for the imaging of structures in the body. The signals produced by the B mode processor are coupled to a scan converter 30 and a multiplanar reformatter 32. The scan converter 30 arranges the echo signals in the spatial relationship from which they were received in a desired image format. For instance, the scan converter 30 may arrange the echo signal into a two dimensional (2D) sector-shaped format, or a pyramidal three dimensional (3D) image. The multiplanar reformatter 32 can convert echoes which are received from points in a common plane in a volumetric region of the body into an ultrasonic image of that plane, as described in U.S. Pat. No. 6,443,896 (Detmer). A volume renderer 34 converts the echo signals of a 3D data set into a projected 3D image as viewed from a given reference point, e.g., as described in U.S. Pat. No. 6,530,885 (Entrekin et al.) The 2D or 3D images are coupled from the scan converter 30, multiplanar reformatter 32, and volume renderer 34 to an image processor 36 for further enhancement, buffering and temporary storage for display on an image display 38. The graphics processor 40 can generate graphic overlays for display with the ultrasound images (e.g., ultrasound image 52). These graphic overlays can contain, e.g., standard identifying information such as patient name, date and time of the image, imaging parameters, and the like. For these purposes the graphics processor 40 receives input from the user interface 24, such as a typed patient name. The user interface can also be coupled to the multiplanar reformatter 32 for selection and control of a display of multiple multiplanar reformatted (MPR) images.

In addition to imaging, the ultrasound imaging system 10 may be configured to measure an attenuation coefficient and/or coefficients for an imaged object. For example, the ultrasound imaging system may include a pulse sequence generator 42, which may be coupled to the transmit controller 20. The pulse sequence generator 42 may provide commands to the transmit controller 20 which then controls the voltage and sequence of firing of the elements of the transducer 14 to transmit ultrasound pulses in accordance with a desired pulse sequence. For example, the pulse sequence may include a wideband pulse and one or more narrowband pulses. In some embodiments, the pulse sequence to be applied by transmit controller 20 may be selected or configured by a user via the user interface 24. The user may manually input the pulse sequence, for example by inputting the number of additional narrowband pulses and specifying the center frequencies, duration, and/or order of the pulses, and/or select a pulse sequence from a set of preprogrammed pulse sequences. The set of preprogrammed sequences provided to the user may be based, at least in part, on the properties of the transducer 14 of the ultrasound imaging system 10. The set of preprogrammed sequences provided may vary as different types of probes or transducers are coupled to and/or activated by the ultrasound imaging system 10. The pulse sequence generator 42 may generate commands based on the selected pulse sequence and/or manually input pulse sequence by the user. In some embodiments, a default pulse sequence may be preprogrammed in the ultrasound imaging system 10.

The pulse sequence for measuring the attenuation coefficient may be applied before or after an ultrasound pulse sequence and/or sequences for B-mode imaging and/or other imaging modes (e.g., M-mode, Doppler, etc.) are applied. The pulse sequence may also include pulses for B-mode imaging and/or other imaging modes. In some embodiments, pulse sequences applied for measuring the attenuation coefficient and imaging may be applied in an interleaved manner. The attenuation coefficient or other information derived based on the attenuation coefficient, such as tissue characterization, collectively referred to as attenuation coefficient information 54, may additionally or alternatively be displayed on the display 38. In some examples, the graphical representation of the attenuation coefficient 54 may be displayed concurrently with the related ultrasound image 52, for example as overlay or in a side by side arrangement. In some embodiments, the attenuation coefficient information 54 may be provided to a different output device (e.g., a printer, included in a report, stored in a storage device, etc.) without necessarily displaying it on the display 38.

The received echoes responsive to the pulse sequence may be provided to the main beamformer 22 and signal processor 26. The signal processor 26 can process the received echo signals from the pulse sequence in various ways, such as bandpass filtering, signal compounding, and noise elimination. The processed signals may be provided to an attenuation coefficient calculator 44. The attenuation coefficient calculator 44 may calculate a value of the attenuation coefficient based on spectral-shift methods, such as the spectral-shift method described in reference to Equation 6. In some embodiments, the attenuation coefficient calculator 44 may further calculate a tissue characterization based on the attenuation coefficient. For example, if the attenuation coefficient is over a threshold value, the attenuation coefficient calculator 44 may characterize the tissue as fatty liver tissue rather than normal liver tissue. In another example, the attenuation coefficient calculator 44 may calculate a percentage of fat in liver tissue, based at least in part on the attenuation coefficient. In these examples, determination of the type of tissue or percentage of fat in liver tissue corresponding to the attenuation coefficient may be based, at least in part, on ex vivo data and/or other methods (e.g., phantoms, simulations). In some embodiments, the attenuation coefficient calculator 44 may calculate an attenuation coefficient and/or tissue characterization for each pixel and/or voxel in a corresponding image acquired by the ultrasound imaging system 10.

In an alternative embodiment, the attenuation coefficient calculator 44 may receive the echo signals of the pulse sequence from the beamformer 22 rather than signal processor 26. The attenuation coefficient calculator 44 may calculate the attenuation coefficient from the unprocessed echo signals and/or perform its own signal processing. Although shown as separate components, the attenuation coefficient calculator 44 and the signal processor 26 may be implemented as a single component in some embodiments. In some embodiments, the signal processor 26 may be implemented as two separate signal processors, where one signal processor processes echoes for B-mode imaging and the other signal processor processes echoes for measuring the attenuation coefficient. In some embodiments, the pulse sequence generator 42 and the attenuation coefficient calculator 44 may be implemented as a single component. In some instances, combining the pulse sequence generator 42 and attenuation coefficient calculator 44 in a single component may facilitate adapting existing ultrasound imaging systems to operate according to principles of the present disclosure.

The calculated attenuation coefficient and/or tissue characterization may be provided by the attenuation coefficient calculator 44 to the graphics processor 40 for presentation on display 38. The attenuation coefficient and/or tissue characterization may be displayed concurrently with an image acquired by the ultrasound imaging system 10. For example, the attenuation coefficient and/or tissue characterization may be displayed as a graphical overlay in a similar manner to patient data and imaging parameters described above. In some embodiments, the graphics processor 40 may provide a color and/or grayscale overlay where each color or shade corresponds to a different attenuation coefficient and/or tissue characterization value or range of values for each pixel or voxel of the image. This may provide a qualitative visualization of attenuation coefficients and/or tissue characterizations of the imaged object.

In some examples, the pulse sequence provided by the pulse sequence generator 42 could be a frequency sweep (e.g., separate pulses for each frequency desired) over a wide range of frequencies. The frequency sweep could be used to establish an equalized power spectrum, $\Phi(f; x, z)$, with a wide frequency range which may reduce variance in attenuation coefficient calculations. However, the length of time to complete such a sweep may be impractical, especially if real-time or near real-time imaging is desired, although not outside of the scope of the present disclosure. Furthermore, using such a sweep may prevent the application of spatial compounding in real time or near real time. Spatial compounding may reduce artifacts, in some embodiments, thus, spatial compounding may be used in both the lateral and the elevational direction when using matrix array transducers to achieve improved performance.

As described, a system according to the present disclosure may be configured to control an ultrasound transducer to transmit pulses in accordance with one or more pulse sequences, at least one of which may be used to acquire echo signals for measuring attenuation coefficient(s) of a medium, and which may then be used e.g., for tissue characterization. For example, the system may control the transducer to transmit pulses according to a first sequence and may additionally optionally control the transducer to transmit pulses according to a second sequence. The first sequence may include at least one wideband pulse within the main passband of the transducer and one or more, in some cases two or more, narrowband pulses outside of the main passband of the transducer. The second sequence may include one or more pulses configured to acquire echo signals for generating imaging data and may thus be configured according to conventional techniques for different modes of imaging (e.g., B-mode, M-mode, Doppler, etc.).

In summary, an ultrasound system according to the present disclosure may include an ultrasound transducer configured to transmit ultrasound pulses toward a medium, such as tissue (e.g., liver tissue). The ultrasound pulses may be transmitted in accordance with a first pulse sequence including one or more pulses inside a main passband of the ultrasound transducer and one or more pulses outside the main passband of the ultrasound transducer. The ultrasound transducer may also transmit ultrasound pulses in accordance with a second pulse sequence. A pulse sequence generator may generate commands corresponding to the first pulse sequence and transmit the commands to a transmit controller. This may cause the ultrasound transducer to transmit the first pulse sequence. An attenuation coefficient calculator may be included in the ultrasound system. The attenuation coefficient calculator may calculate an attenuation coefficient of the medium based, at least in part, on echo signals received responsive to the first pulse sequence. A processor configured to generate ultrasound imaging data based on echo signals received responsive to the second pulse sequence may also be included in the system.

Figure 2:
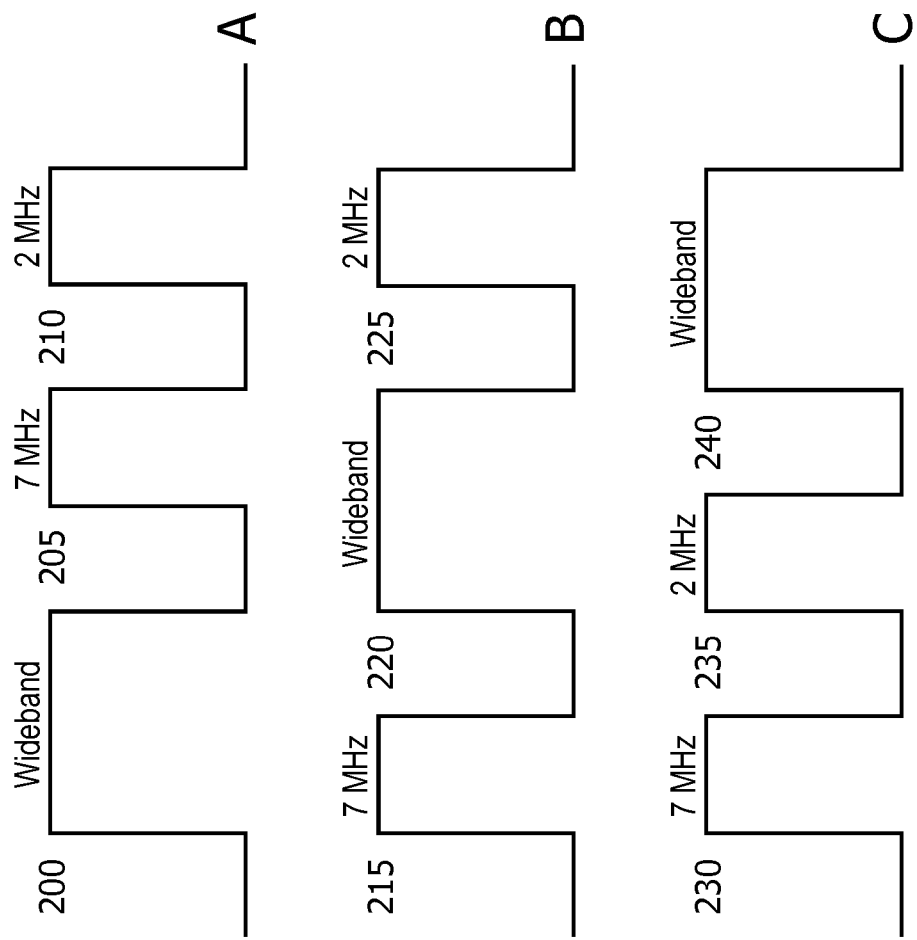
FIG. 2 illustrates example pulse sequences according to embodiments of the disclosure.

FIG. 2 illustrates examples of pulse sequences which may be generated by a system according to principles of the present disclosure, e.g., for measuring attenuation coefficients. FIG. 2 illustrates three example pulse sequences A-C each including three pulses, Sequence A includes pulses 200, 205, and 210, Sequence B includes pulses 215, 220, and 225, and Sequence C includes pulses 230, 235, and 240. The width of the pulses 200-240 qualitatively (that is, not to scale) illustrates the frequency range of each pulse. For example, pulse 200 in Sequence A has a broader frequency range than pulses 205 and 210. The order of the pulses 200-240 in each sequence represents when in time each pulse is transmitted relative to the other pulses in the sequence. For example, in Sequence A, pulse 200 is transmitted prior to pulse 205, and pulse 205 is transmitted prior to pulse 210. The Sequences A-C illustrated in FIG. 2 may be transmitted by a transducer which has a main passband (e.g., −6 dB passband) between within a given range of frequencies, e.g., 3 and 6 MHz. For each transducer element the transducer is controlled to transmit three pulses based on the commands sent for example from a pulse sequence generator to a transmit controller operably coupled to the transducer. In Sequence A, the first transmit pulse 200 is a wideband pulse, the second 205 is a narrowband pulse centered at 7 MHz, and the third 210 is narrowband pulse centered at 2 MHz. However, the pulse sequence is not limited to the wideband pulse transmitted first. As shown in Sequence B, the first pulse 215 is a narrowband pulse centered at 7 MHz, the second pulse 220 is a wideband pulse, and the third pulse 225 is a narrowband pulse centered at 2 MHz. In Sequence C, the two narrowband pulses 230 and 235 are transmitted prior to the wideband pulse 240. Furthermore, the narrowband pulse with a lower center frequency (e.g., pulses 210, 225, and 235) may be transmitted prior to the narrowband pulse with a high center frequency (e.g., pulses 205, 215, and 230).

The wideband pulse (e.g., pulses 200, 220, and 240) may have a bandwidth of 2 MHz in the example provided in FIG. 2. Depending on properties of the transducer (e.g., width of the main passband, driving limits of the transducer elements), the wideband pulse may have a bandwidth of 1-3 MHz in other embodiments. In the example provided in FIG. 2, the narrowband pulses may have a bandwidth of 10-100 kHz. Depending on the properties of the transducer, in other embodiments, the narrowband pulses may have a bandwidth of 1 kHz-300 kHz.

To improve the SNR, the narrowband pulses may be longer in the time domain than the wideband pulse. That is, the transmission time of the narrowband pulses may be greater than the transmission time of the wideband pulse. For example, the wideband pulse may be 0.5 μs-1.0 μs in length whereas the narrowband pulses may be 10 μs in length. The time duration of the narrowband pulses may be longer or shorter, based at least in part, on the desired SNR and/or energy transmission at the desired frequencies.

Although three pulses are shown in the sequences illustrated in FIG. 2, sequences may have more or fewer pulses. For example, only a wideband pulse and a narrowband pulse with a high center frequency may be transmitted. In another example, a sequence may include a wideband pulse, a narrowband pulse with a low center frequency, and two narrowband pulses with different high center frequencies (e.g., 6.5 MHz and 7.5 MHz). Furthermore, the provided frequency ranges of the wideband and narrowband pulses are merely exemplary. The center frequencies and frequency ranges of the pulses may be different for an ultrasound transducer having different properties, such as a different main passband frequency range. The center frequencies and frequency ranges of the pulses may be different for different ultrasound imaging applications. For example, for deep tissue imaging, lower center frequencies may be selected relative to the center frequencies selected for superficial tissue imaging.

The pulses in FIG. 2 are illustrated as having square spectral shape. However, the pulses may have rounded edges, sloping edges, and/or a sinusoidal appearance in the frequency domain. Similarly, the pulses may not be square in the time domain. The pulses may have rounded edges, sloping edges, and/or a sinusoidal appearance in the time domain.

FIG. 2 illustrates sequences where the narrowband pulses are transmitted separately. However, it is possible to transmit multiple narrowband pulses at the same time rather than sequentially. For example, a transducer may have a main passband (e.g., −6 dB passband) between 3 and 6 MHz. For each transmit beam, the transducer transmits two pulses. The first transmitted pulse is a wideband pulse, and the second pulse is a sum of two narrowband pulses with 2 MHz and 7 MHz center frequencies. More than two narrowband pulses may be combined in a single pulse, but there may be a limit to the number of narrowband pulses that may be combined in a single pulse. The limit may be based on the voltage limit, main passband range, and/or other properties of the transducer. The narrowband pulses may be shifted in phase to increase the energy available to be transmitted at each frequency of the narrowband pulses and/or increase the number of narrowband pulses that may be transmitted in a single pulse.

As an alternative to a simple pulse sequence, coded excitation may be used. Coded excitation of ultrasound signals may increase the total transmitted energy without exceeding safety limits for medical ultrasound. Coded excitation in ultrasound is analogous to coded excitation in other fields (e.g., frequency modulation (FM) radio). Appropriate coding of the pulses is required on transmitting and appropriate decoding is required on receiving the echo signals. Coding of the ultrasound pulses may be provided by commands generated by a pulse sequence generator and decoding of the echo signals may be provided by an attenuation coefficient calculator, such as pulse sequence generator 42 and attenuation coefficient calculator 44 in FIG. 1, respectively. In some embodiments, some or all of the decoding may be provided by a signal processor, such as signal processor 26 in FIG. 1.

Coded excitation, such as linear chirps, is commonly used for improving SNR in ultrasound imaging. However, for measuring attenuation coefficient, enhancing frequency components outside the transducer's main passband to increase the working bandwidth of the transducer is desired. Therefore, nonlinear chirps may perform better than linear chirps in attenuation coefficient estimation in some applications.

Figure 3:
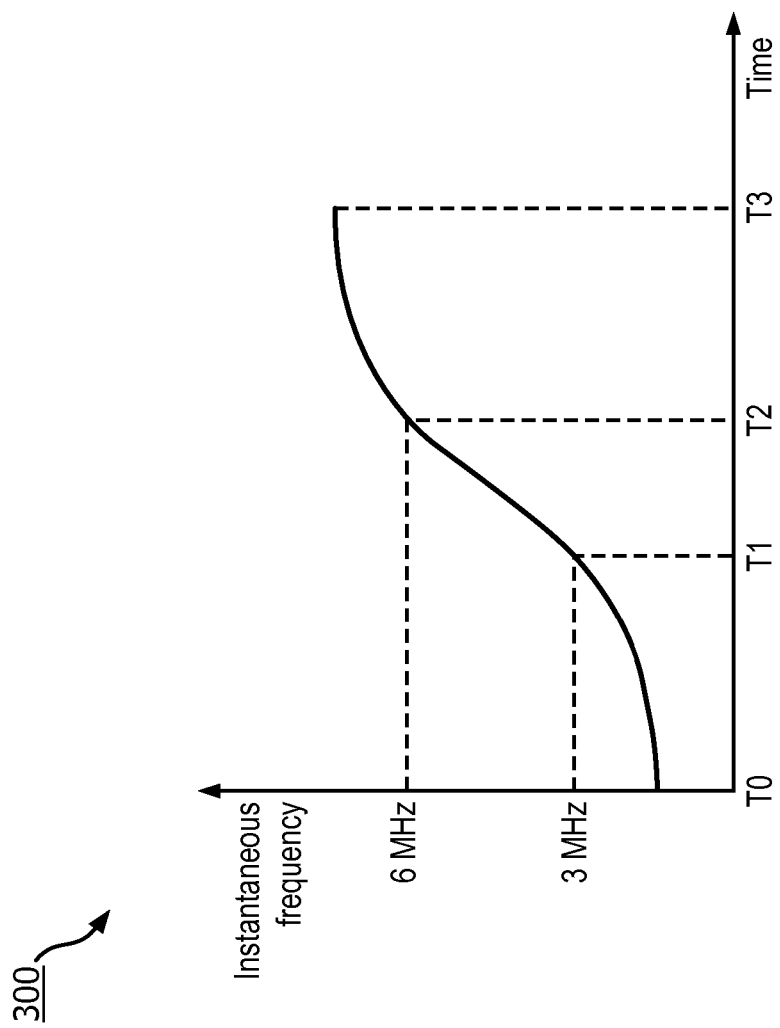
FIG. 3 illustrates an example coded excitation according to an embodiment of the disclosure.

FIG. 3 illustrates an example of a nonlinear chirp according to principles of the present disclosure. The nonlinear chirp may be transmitted by an ultrasound transducer based on commands provided by a pulse sequence generator. The y-axis represents the frequency of the transmitted signal, and the x-axis represents time. In the example illustrated in FIG. 3, the transducer transmitting the coded excitation has a main passband from 3 MHz to 6 MHz. The nonlinear chirp may approximate a cascade of: a low-frequency narrowband pulse at the beginning of the transmission, a wideband pulse in the middle, and a high-frequency narrowband-pulse at the end of the transmission. In some embodiments, the nonlinear chirp phase response may be piece-wise quadratic such that in the time domain, the signal has constant amplitude over the duration of the chirp. The nonlinear chirp from T0 to T1 may correspond to a low-frequency narrowband pulse. The time duration from T0 to T1 may be from 5-20 µs. The nonlinear chirp from T1-T2 may correspond to a wideband pulse. The time duration from T1-T2 may be 1-3 µs. The nonlinear chirp from T2 to T3 may correspond to a high-frequency narrowband pulse. The time duration from T2 to T3 may be 5-20 µs. The time durations provided are for exemplary purposes. Other time durations may be used for the nonlinear chirp. The total time duration of the nonlinear chirp may be between 10 µs and 1 ms. The total time duration may be based, at least in part, on properties of the transducer, the object being imaged, the depth of the object, and/or the coded excitation technique being applied. Typically the time duration of the signal outside the main passband of 3 MHz to 6 MHz is greater than the time duration of the signal within the main passband. This may improve the SNR for signals outside the main passband of the transducer, which may improve attenuation coefficient calculations.

As described herein, a method for determining an attenuation coefficient in tissue may include transmitting ultrasound pulses from an ultrasound transducer (e.g., ultrasound transducer 12) towards a tissue in accordance with a pulse sequence. The pulse sequence may include pulses of at least one first frequency inside and at least one second frequency outside a main passband of the ultrasound transducer. The method may include receiving echo signals that correspond to the pulses of the at least one first and the at least one second frequencies of the pulse sequence and determining (e.g., with the attenuation coefficient calculator 44) an attenuation coefficient of the tissue based, at least in part, on a combination of received echo signals that correspond to the pulses of the at least one first and the at least one second frequencies. An ultrasound image concurrently with the calculated attenuation coefficient may be displayed.

Figure 4:
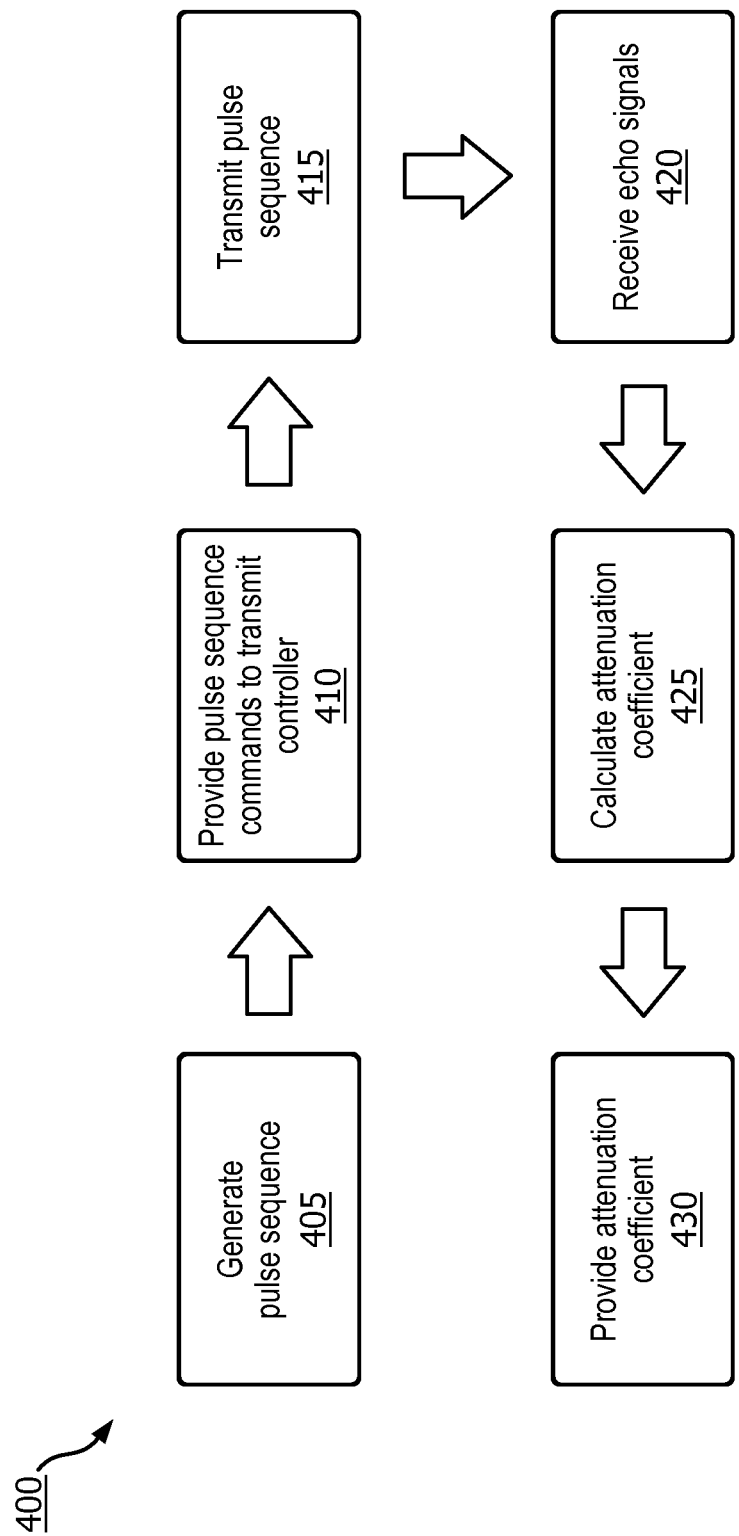
FIG. 4 is a flow chart of a method according to an embodiment of the disclosure.

FIG. 4 is a flowchart of a method 400 according to principles of the disclosure. The flow chart summarizes a method for improving acoustic attenuation coefficient measurements according to the methods and examples described herein. At Step 405, a pulse sequence may be generated. The pulse sequence may be a series of pulses as described in reference to FIG. 2 or coded excitation as described in reference to FIG. 3. The pulse sequence may be generated by a pulse sequence generator, such as pulse sequence generator 42 in FIG. 1. At Step 410, commands for the pulse sequence may be provided to a transmit controller, such as transmit controller 20 in FIG. 1. The transmit controller may control the transmission of an ultrasound transducer, such as ultrasound transducer 14 in FIG. 1. The transducer may transmit the pulse sequence at Step 415 and receive the resulting echo signals at Step 420.

The received echo signals may be provided to an attenuation coefficient calculator, such as attenuation coefficient calculator 44 in FIG. 1. At Step 425, the attenuation coefficient calculator may calculate an attenuation coefficient based, at least in part, on the received echo signals. The attenuation coefficient calculator may calculate the attenuation coefficient using spectral-shift methods or hybrid methods based on both spectral shift and spectral difference. For example, the attenuation coefficient calculator may use the spectral-shift method described in reference to Equation 6. At Step 430, the calculated attenuation coefficient may be provided to a graphics processor for display, such as graphics processor 40 in FIG. 1. As discussed previously, in some embodiments, the attenuation coefficient calculator may calculate a tissue characterization based, at least in part, on the attenuation coefficient, at Step 425. The tissue characterization may be provided to the graphics processor at Step 430.

Figure 5:
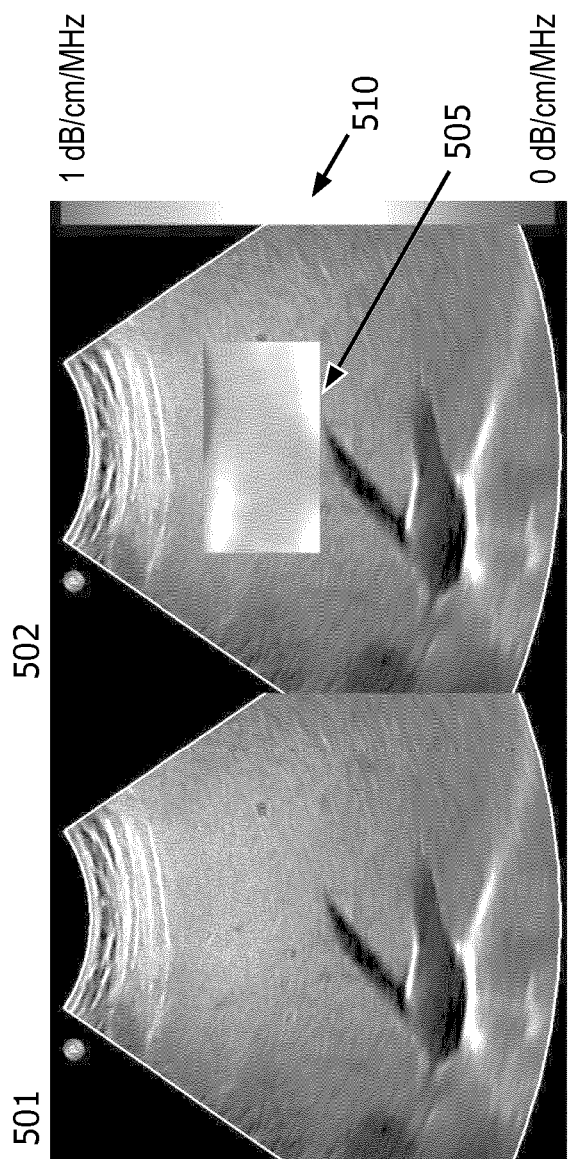
FIG. 5 illustrates example ultrasound images according to an embodiment of the disclosure.

FIG. 5 illustrates example ultrasound images 501 and 502 according to embodiments of the disclosure. Images 501 and 502 may be displayed individually or concurrently as shown in FIG. 5. The images 501 and 502 may be provided on a display, such as display 38 in FIG. 1. Image 501 is a B-mode image of a portion of a liver. Image 501 may have been generated by an image processor (e.g., image processor 36). Image 502 is the same B-mode image of the portion of the liver with attenuation coefficient information displayed concurrently. As shown in image 502, the attenuation coefficient information includes an attenuation coefficient map 505 overlaid on the B-mode image. In the example shown in image 502, the attenuation coefficient map 505 is a color-coded map wherein each pixel is colored based on the attenuation coefficient value calculated for the corresponding pixel in the B-mode image. In other embodiments, the attenuation coefficient map 505 may be implemented as a grayscale map. Although shown covering only a portion of the B-mode image in image 502, in some embodiments, the attenuation coefficient map 505 may overlay the entire B-mode image. The scale bar 510 shows which colors correspond to what value and/or range of values of attenuation coefficient. The scale bar 510 in this example ranges from 0 dB/cm/MHz to 1 dB/cm/MHz. Depending on the frequency and/or tissue type, other ranges may be displayed. In some embodiments, the attenuation coefficient map 505 may be generated by a graphics processor (e.g., graphics processor 40) based at least in part on attenuation coefficient information received from an attenuation coefficient calculator (e.g., attenuation coefficient calculator 44).

The attenuation coefficient map 505 may provide a qualitative overview of the range of attenuation coefficients in a tissue. In some embodiments, individual attenuation coefficient values may be provided for each pixel. The attenuation coefficient information may be provided in a separate file, provided on an alternative display, and/or displayed concurrently with the B-mode image and/or B-mode image overlaid with the attenuation coefficient map. In some embodiments, individual attenuation coefficient values for individual pixels may be displayed on image 502 and/or adjacent to image 502. The individual values for display may be determined by a cursor pointing to a particular pixel and/or an individual pixel being selected (e.g., coordinates provided via a user interface). Other variations of displaying the attenuation coefficient information with ultrasound images may also be used. For example, the maximum and minimum attenuation coefficient values may be displayed on or adjacent to the ultrasound image. In another example, a histogram of attenuation coefficient values may be displayed on or adjacent to the ultrasound image.

The application of pulse sequences described herein may improve SNR for frequencies outside the main passband of ultrasound transducers. This may allow for signals from a broader range of frequencies to be used to calculate an acoustic attenuation coefficient. The broader frequency range may reduce the variance, and thus improve the accuracy, of attenuation coefficients. As attenuation coefficients become more reliable, they may allow for quantitative analysis or diagnosis of conditions in medical imaging.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system has been described with reference to an ultrasound imaging system, the present system may be extended to other imaging systems that use spectral-shift methods for calculating attenuation coefficient. Additionally, the present system may be used to obtain and/or record image information related to, but not limited to renal, testicular, prostate, breast, ovarian, uterine, thyroid, hepatic, lung, musculoskeletal, splenic, nervous, cardiac, arterial and vascular systems, as well as other imaging applications. Further, the present system may also include one or more elements which may be used with non-ultrasound imaging systems with or without real-time imaging components so that they may provide features and advantages of the present system.

Further, the present methods, systems, and apparatuses may be applied to existing imaging systems such as, for example, ultrasonic imaging systems. Suitable ultrasonic imaging systems may include a Philips® ultrasound system which may, for example, support a conventional broadband linear array transducer that may be suitable for small-parts imaging.

Certain additional advantages and features of this invention may be apparent to those skilled in the art upon studying the disclosure, or may be experienced by persons employing the novel system and method of the present invention, chief of which is lower variance when measuring acoustic attenuation coefficient. Another advantage of the present systems and method is that conventional medical imaging systems may be easily upgraded to incorporate the features and advantages of the present systems, devices, and methods.

Of course, it is to be appreciated that any one of the above embodiments or processes may be combined with one or more other embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. A method for determining an attenuation coefficient of tissue, the method comprising:
    transmitting ultrasound pulses from an ultrasound transducer towards a tissue in accordance with a pulse sequence, the pulse sequence including pulses of at least one first frequency inside and at least one second frequency outside a main passband of the ultrasound transducer, wherein the pulse of at least one first frequency is within a wideband pulse range and the pulse of at least one second frequency is within a narrowband pulse range;
    receiving echo signals that correspond to the pulses of the at least one first and the at least one second frequencies of the pulse sequence;
    determining an attenuation coefficient of the tissue based, at least in part, on a combination of received echo signals that correspond to the pulses of the at least one first and the at least one second frequencies; and
    displaying an ultrasound image concurrently with the calculated attenuation coefficient.

2. The method of claim 1, wherein the ultrasound image is generated from echoes received from a second pulse sequence.

3. The method of claim 1, wherein the calculated attenuation coefficient is displayed as a map overlaying the ultrasound image.

4. The method of claim 3, wherein the map is a color map.

5. The method of claim 1, wherein a center frequency of the pulse of at least one first frequency is within the main passband of the ultrasound transducer.

6. The method of claim 1, wherein a center frequency of the pulse of at least one second frequency is outside the main passband of the ultrasound transducer.

7. The method of claim 1, wherein the pulse of at least one second frequency is a combination of a plurality of narrowband pulses having different center frequencies.

8. The method of claim 7, wherein phases of the plurality of narrowband pulses having different center frequencies are shifted with respect to one another.

9. The method of claim 1, wherein a time duration of the pulse of at least one first frequency is less than a time duration of the pulse of at least one second frequency.

10. The method of claim 1, wherein the pulse sequence comprises a coded excitation.

11. The method of claim 10, wherein the coded excitation includes a nonlinear chirp.

12. The method of claim 1, wherein determining the attenuation coefficient includes a spectral-shift method.

13. An ultrasound imaging system comprising:
    an ultrasound transducer configured to transmit ultrasound pulses toward a tissue, wherein the ultrasound pulses are transmitted in accordance with a pulse sequence, the pulse sequence including pulses of at least one first frequency inside and at least one second frequency outside a main passband of the ultrasound transducer, wherein the pulse of at least one first frequency comprises a wideband pulse and the pulse of at least one second frequency comprises at least one narrowband pulse;
    an attenuation coefficient calculator circuit configured to calculate an attenuation coefficient of the tissue based, at least in part, on echo signals that correspond to the pulses of the at least one first and the at least one second frequencies; and
    at least one processor circuit configured to generate ultrasound imaging data based on the echo signals.

14. The ultrasound imaging system of claim 13, wherein the ultrasound transducer is a CMUT or a piezoelectric transducer.

15. The ultrasound imaging system of claim 13, wherein the attenuation coefficient calculator circuit is further configured to calculate a tissue characterization based, at least in part, on the attenuation coefficient of the medium.

16. The ultrasound imaging system of claim 13, further comprising a pulse sequence generator configured to:
    generate commands corresponding to the pulse sequence; and
    transmit the commands to cause the ultrasound transducer to transmit the pulse sequence.

17. The ultrasound imaging system of claim 16, wherein the pulse sequence generator is further configured to generate a coded excitation.

18. The ultrasound imaging system of claim 17, wherein the attenuation coefficient calculator circuit is further configured to decode echo signals resulting from the coded excitation.

19. The ultrasound imaging system of claim 13, further comprising a signal processor circuit configured to receive the echo signals, process the echo signals, and provide the processed signals to the attenuation coefficient calculator circuit.

* * * * *